United States Patent [19]
Silverman et al.

[11] Patent Number: 5,776,068
[45] Date of Patent: Jul. 7, 1998

[54] ULTRASONIC SCANNING OF THE EYE USING A STATIONARY TRANSDUCER

[75] Inventors: Ronald H. Silverman, Brooklyn, N.Y.; Donald Jackson Coleman, Haworth, N.J.; Dan Z. Reinstein, New York, N.Y.; George Simoni, Teaneck, N.J.; David Najafi, New York, N.Y.

[73] Assignee: Cornell Research Foundation, Ithaca, N.Y.

[21] Appl. No.: 879,292

[22] Filed: Jun. 19, 1997

[51] Int. Cl.⁶ .................................................. A61B 8/00
[52] U.S. Cl. .................................. 600/443; 600/452
[58] Field of Search .................................. 600/443, 452, 600/558

[56] References Cited

U.S. PATENT DOCUMENTS

| | | | |
|---|---|---|---|
| 4,484,569 | 11/1984 | Driller et al. | 600/452 X |
| 4,856,891 | 8/1989 | Pfibsen | 351/210 |
| 4,934,370 | 6/1990 | Campbell | 600/452 |
| 5,070,883 | 12/1991 | Kasahara | 128/745 |
| 5,293,871 | 3/1994 | Reinstein | 128/660.06 |
| 5,331,962 | 7/1994 | Coleman et al. | 600/452 X |
| 5,369,454 | 11/1994 | Reinstein et al. | 600/447 X |

OTHER PUBLICATIONS

Reinstein et al. "Corneal Pachymetric Topography", Ophthalmology. vol. 101, 3, Mar. 1994, pp. 432–438.

*Primary Examiner*—Francis Jaworski
*Attorney, Agent, or Firm*—Olhlandt, Greeley, Ruggiero & Perle

[57] ABSTRACT

Apparatus is provided for high frequency ultrasound examination of the anterior segment of a patient's eyes. A liquid bath is established about a first eye of the patient to be examined. A fixed ultrasound transducer is placed in contact with the liquid bath and directs the beam of ultrasound energy to the first eye and receives echoes of the ultrasound energy. A fixation source is juxtaposed to the second eye of the patient and displays a fixation target. A controller operates the fixation source to move the fixation target relative to the second eye, while the patient moves the second eye so as to remain focused on the fixation target. The movement of the second eye causes the first eye to move concurrently and enables relative movement between the beam of ultrasound energy and anterior segments of the first eye, while maintaining near orthogonality between the ultrasound beam and the surface of the eye. By tracking the position of the second eye, the position of the first eye, and hence of each pulse/echo sequence, is ascertained, enabling image construction and biometric determinations of the anterior segment anatomy to be performed.

9 Claims, 2 Drawing Sheets

ULTRASONIC SCANNING OF THE EYE USING A STATIONARY TRANSDUCER

This invention was made with Government support under Grant No. EY03183, awarded by the National Institutes of Health. The Government has certain rights in the invention.

FIELD OF THE INVENTION

This invention relates to ultrasonography and, more particularly, to an ultrasonic device for examining anterior portions of the eye.

BACKGROUND OF THE INVENTION

Prior art high frequency, ophthalmic, ultrasound systems scan the curved surface of anterior segments of the eye by linearly translating an ultrasonic transducer. Two systems incorporating high frequency, linearly translatable transducers have been developed. One is called the ultrasound biomicroscope and is produced by Humphrey Instruments, San Leandro, Calif. The ultrasound biomicroscope obtains data by oscillatory linear motion of a focused transducer over a fixed distance. The transducer assembly is manually positioned while scanning takes place and the image appears on a video display. The acoustic signal envelope is determined by analog circuitry and is converted to a video format that is then displayed and/or stored.

A further system is described in U.S. Pat. No. 5,369,454 to Reinstein et al. and assigned to the same Assignee as this Application, mounts the ultrasound transducer on a pair of linear positioners that are at right angles to each other. During scanning, radio frequency echo data are digitized at a rate well above the Nyquist rate and images are constructed from the stored radio frequency data. This action allows enhancement and analysis of the data through the use of digital signal processing techniques. The use of two linear positioners allows data to be obtained in sequential, parallel scan planes from which three dimensional images are constructed.

Both the ultrasound biomicroscope and the ultrasound scanner disclosed in U.S. Pat. No. 5,369,454 scan the eye using linear translation of the transducer. The curved specular surfaces of the eye, especially the cornea, result in significant signal loss as the angle of the surface departs from the normal to the transducer axis. For this reason, data acquired by linear scanning are limited to an area of 3–3.5 mm in diameter of cornea and images of the anterior segment to one quadrant at a time.

This problem is addressed in U.S. Pat. No. 5,293,871 to Reinstein et al., assigned to the same Assignee as this application, wherein a mechanical scan system is disclosed for moving a transducer in an arc, such that both normality and range remain approximately constant over the full extent of the cornea. The Reinstein et al '871 patent further employs a fixation point upon which the eye not being examined can focus. Accordingly, the eye being examined is maintained in a fixed orientation and in alignment with the eye focused on the fixation point.

In the '454 Reinstein et al. patent, a light source is positioned above a liquid bath in which the patient's eye is submerged. A beam of alignment light is directed at the submerged eye and another light source is positioned above the patient's second eye. The second light source is moved until the patient indicates a fusion of the light sources into a single spot, at which point it is known that the visual axis of the eyes are vertical and aligned. Thereafter, the submerged eye is subjected to an ultrasound scan.

The advent of excimer laser, corneal re-profiling has revolutionized the practice of kerato-refractive procedures. Such procedures alter normal eyes with a surgical procedure and are accompanied by a small but measurable risk of scarring, with loss of vision. To choose the best method for managing the complications of refractive surgery, it is necessary to monitor the cornea and anterior segment in a highly anatomically accurate manner. Scanning before and after the operative procedure can also provide unique information as to the cause of failure to reach an intended refractive change, in that changes in the individual corneal layers during healing can cause unpredicted shifts in ocular refraction.

Accordingly, it is an object of this invention to provide an improved ultrasound imaging system, particularly adapted to 3-D imaging of corneal structures and the anterior segments of the eye.

SUMMARY OF THE INVENTION

Apparatus is provided for ultrasonically examining a patient's eyes, the patient being in generally supine position. A liquid bath is established about a first eye of the patient to be examined. A fixed ultrasound transducer is placed in contact with the liquid bath and directs the beam of ultrasound energy to the first eye and receives echoes of the ultrasound energy. A fixation source is juxtaposed to the second eye of the patient and displays a fixation target. A controller operates the fixation source to move the fixation target relative to the second eye, while the patient moves the second eye so as to remain focused on the fixation target. The movement of the second eye causes the first eye to move concurrently and enables relative movement between the beam of ultrasound energy and anterior segments of the first eye.

DETAILED DESCRIPTION OF THE INVENTION

Figure 1:
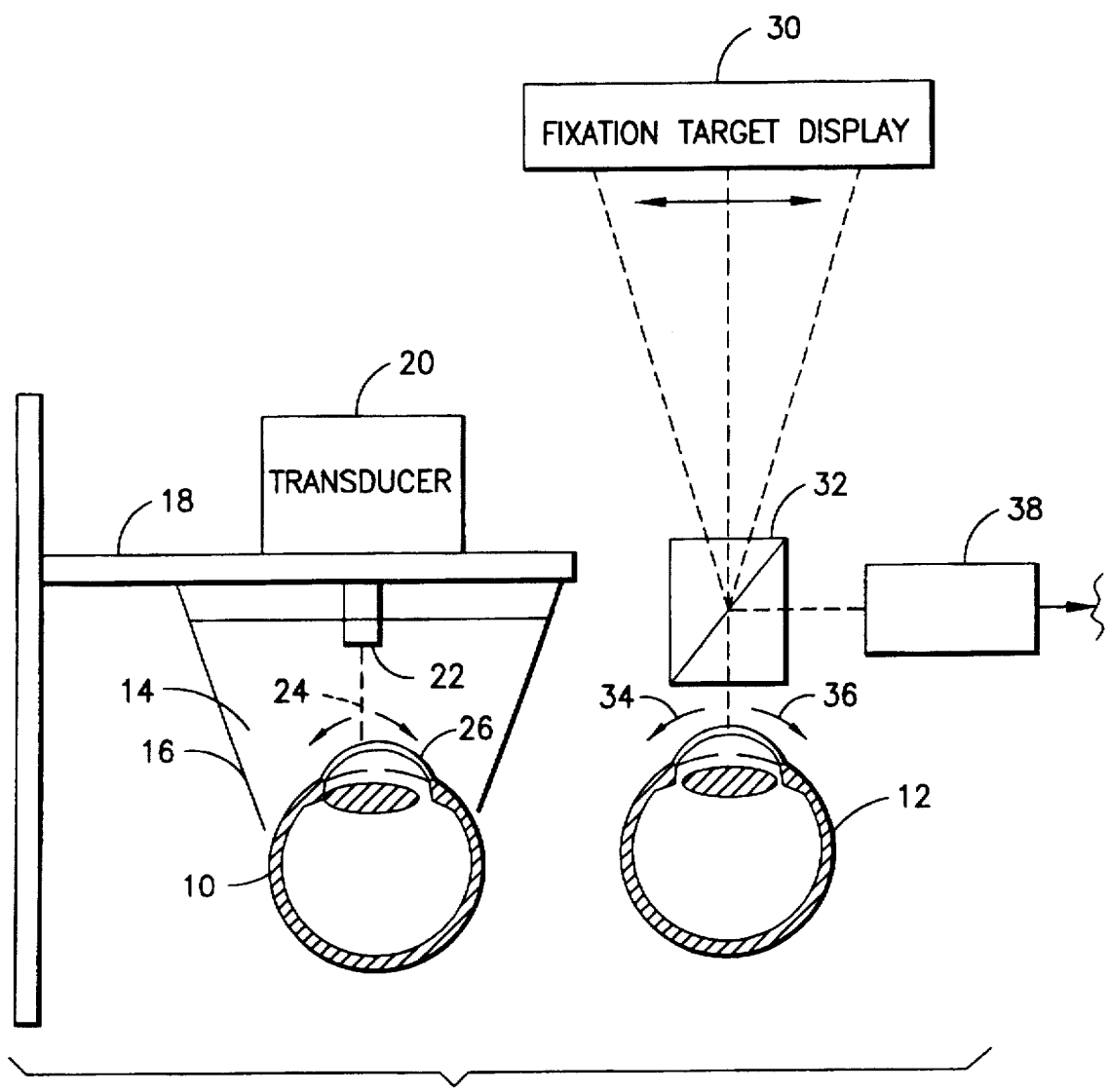
FIG. 1 is a schematic view of apparatus that incorporates the invention.

Referring to FIG. 1, a patient is positioned in the supine position so that the patient's eyes 10 and 12 are directed upwardly. Eye 10, whose anterior segments are to be examined ultrasonically, is provided with a drop of topical anaesthetic and is held open with a lid speculum. A normal saline water bath 14 is established around eye 10 by the use of a sterile drape 16 that is supported by a stand 18. An ultrasonic transducer 20 is rigidly fixed to stand 18 and includes a portion 22 that is submerged in saline bath 14.

In operation, transducer 20 causes the transmission of an ultrasound signal along axis 24 towards anterior segments of eye 10 and, further, receives echoes from the structural segments thereof.

Transducer 20 is preferably fixed in such a manner that axis 24 is normal to the corneal apex. Because the globe defined by the cornea has a radial dimension of approximately 24 mm, it can be viewed ideally as a sphere with a 12 mm radius of curvature. Thus, by affixing transducer 20 and focusing the ultrasonic beam onto corneal surface 26, the focus of the beam will remain unchanged as eye 10 (and corneal surface 26) is caused to move in a manner that will be described below. By synchronizing ultrasound data acquisition with measurement of the eye position of eye 10. 3-dimensional data are acquired without requiring any movement of transducer 20.

To enable movement of eye 10, advantage is taken of the normal concurrence of a patient's eye movements. More specifically, it is known that movement of one patient's eye is accompanied by a tracking movement of the other patient's eye. Thus, referring to FIG. 1, a fixation target display 30 is positioned over eye 12 and is controlled to display a fixation target thereon which is caused to move through operation of a connected controller. As the image of the fixation target moves across fixation target display 30, its image is projected downwardly through a splitter 32 and onto the corneal surface of eye 12. The patient is instructed to follow the movement of the fixation target and thus moves eye 12 in the directions of arrows 34/36 as the fixation target is moved. As a result, eye 10 moves concurrently with eye 12, enabling a relative motion to be established between the anterior segments of eye 10 and the ultrasound beam.

A camera 38 is positioned to receive an image of the anterior segment of eye 12 and to thereby provide eye tracking signals to a processor (to be described below with regards to FIG. 2), so as to enable a correlation to be achieved between eye position and the echoes received by transducer 20.

Figure 2:
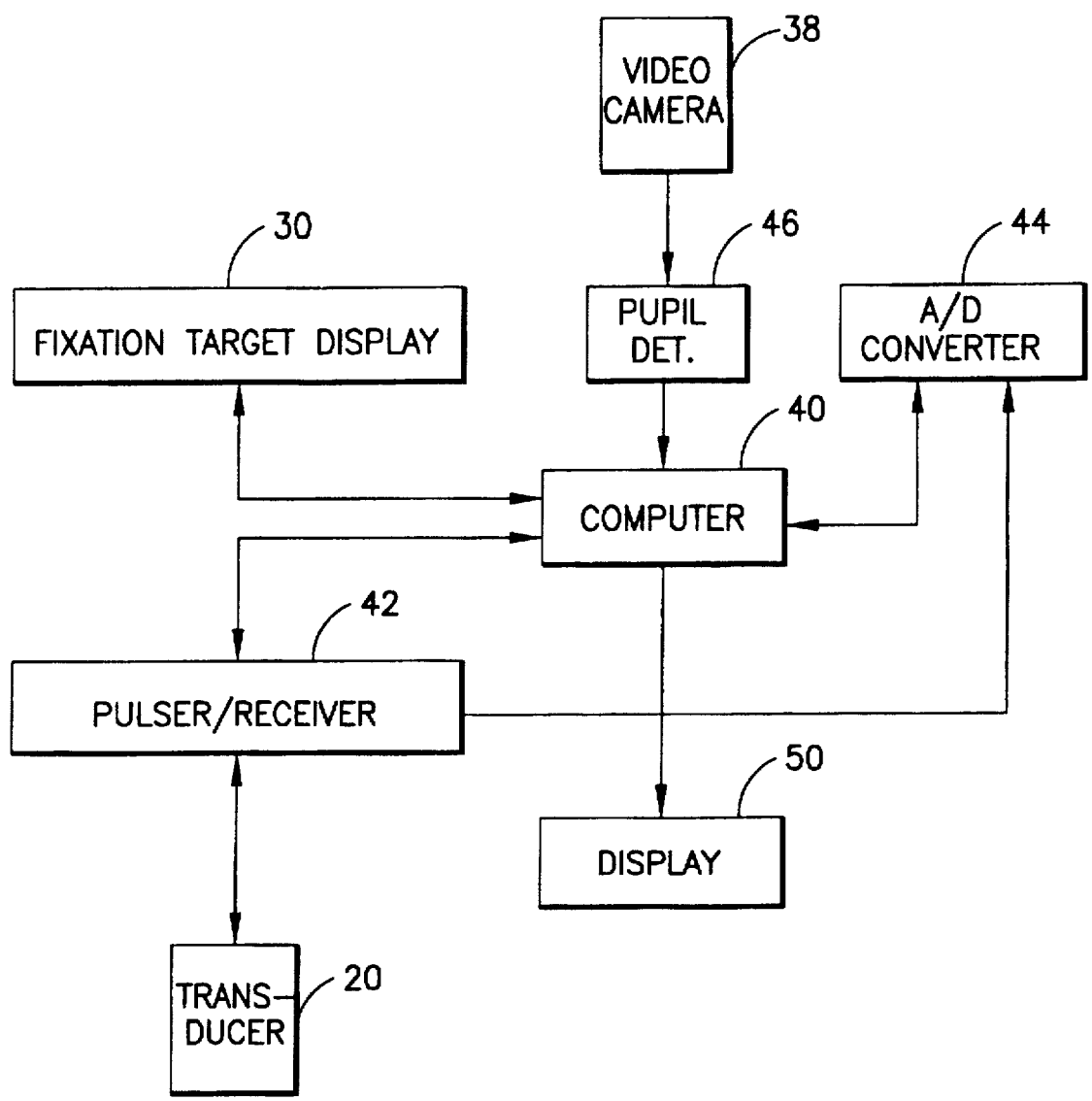
FIG. 2 illustrates a block diagram of electrical portions of the system of FIG. 1.

Referring to FIG. 2, a computer 40 is employed to control both fixation target display 30 and transducer 20. Accordingly, computer 20 causes a scanning of the fixation target by fixation target display 30 and synchronizes therewith, the operation of a pulser/receiver 42. Pulser/receiver 42 controls transducer 20 in the known manner and provides an output to A/D converter 44 wherein analog scan signals are converted to a plurality of sampled digital values. Computer 40 is provided with the digitized values after they are accumulated by A/D converter 44.

Video camera 38 feeds a video image of the anterior of eye 12 to a pupil detector 46. Pupil detector 46 includes a microprocessor and an image buffer which enables successive pupil positions to be determined at regular intervals and signalled to computer 40. At each interval, a trigger pulse is caused to excite pulser/receiver 42, to thereby enable transducer 20 to provide one pulse/echo data sequence at a known position.

Fixation target display 30 is preferably either a video display or a two dimensional array of light emitting diodes. Computer 40 causes a raster type scan to occur across the surface of fixation target display 30 so as to enable a 2-dimensional movement of a fixation target to occur. As the patient's eye 12 follows the movement of the fixation target, pulse/receiver 42 is accordingly controlled to obtain ultrasound echoes returned from the anterior segments of eye 10.

When a full two-dimensional scan of fixation target display 30 has been completed, computer 40 will have acquired sufficient echo data to provide an indication, via display 50 of corneal surface 26 of eye 10.

It is preferred that a 50 MHz polyvinylidene fluoride (PVDF) transducer with a 3 mm aperture and which is spherically focused at about 10 mm, be used. Such a transducer can be obtained from Panametrics, Inc., Waltham, Mass. The transducer is coupled to the eye via a 0.9% saline solution, using either a water bath, goggles or other appropriate instrumentality. The transducer is positioned along the optical axis of the eye so as to place the area of interest (the cornea, iris, etc.) in the focal plane. Positional data is obtained with an eye-tracking board incorporated into a PC type computer. As acquisition takes place, the computer displays the position of each acquiring sequence as a point, superimposed upon an image of the eye.

After acquisition is complete, echo data is transferred to the computer. Each sequence is stored on disk and a header is appended containing the position of the eye at the moment of acquisition. Three-dimensional sequences are obtained, either by moving the fixation target in a regular grid in a raster-like manner, or in a variety of other manners. Two and 3-dimensional images, as well as corneal topographic and pachymetric maps can be produced from the stored data by locating the appropriate scan vectors for each image position and interpolating, as required.

While the description above has indicated that the position of eye 10 can be tracked through the use of camera 38, eye 10 can also be tracked through the use of a fiber optic bundle immersed in saline bath 14 and focused upon corneal surface 26 of eye 10. In this case, the camera viewpoint will be slightly offset from the transducer axis.

As a further embodiment, the entire system is incorporated into head-mounted goggles. The advantages of such a setup include simplicity and the ability to scan the patient in any head position. The latter is of importance for diagnostic imaging of the angle in glaucoma. (The angle is the anatomic region in which fluid outflow from the eye occurs. When outflow is impeded by clogging with debris or narrowing of the angle, an increase in intraocular pressure results, i.e., glaucoma.)

Current ultrasound systems must scan in the supine position, and gravity is known to affect the angle's anatomy. Because the system is lightweight and does not have moving parts, it can be mounted on goggles and the eye scanned in any head position.

Goggles will allow the transducer to be coupled to one eye with a contained normal saline solution, while the other eye is optically tracked. As such, the ultrasound scanning compartment must be watertight, i.e., fluid should not leak into the other eye, down the cheek, etc. This is possible through use of inexpensive off-the-shelf diving goggles. ISCAN (Cambridge, Mass.) manufactures a miniature goggle-mounted camera and optics to allow the subject to see a display while the eye is illuminated (with an infrared source) and is optically tracked.

The goggles allow the transducer to be positioned laterally over a range sufficient to center it over the eye. Initially, a dummy alignment transducer is inserted into a transducer mount. The transducer possesses a central cylindrical aperture, with a light source at its distal end. The position of the transducer mount is then adjusted so that the subject can see the illuminating light. At this point, the video-tracking system is aligned to the optic axis.

The mount is then locked in position, the dummy transducer removed and the ultrasound transducer placed in the same mount. Any subsequent ultrasonic data acquisition is therefore aligned with the visual axis.

Once the transducer is appropriately positioned, the chamber is filled with normal saline (at 33° C.) and the transducer's range is adjusted to place the cornea in the focal plane. This is facilitated by the display of the corneal echo signal on a computer display.

Both ultrasound scanning and eye-tracking require that the eye not be obscured by the eyelids. This is especially true for downward gaze, where the upper lid tends to descend. This problem is addressed by either use of a wire lid speculum (which holds the lids open) or a "crutch". The latter is currently used in patients suffering ptosis, a dropping of the upper lids. This is an attachment to an eyeglass frame that functions as a "hanger" for the upper lid by insertion into the superior orbital sulcus, preventing the lid from drooping. A crutch can be incorporated into the goggle to prevent drooping of the upper lid on downward gaze.

As can be seen from the above, the ultrasound imaging system incorporating the invention includes no moving parts and thereby exhibits decreased complexity and cost. Further, there is no need to rely on the patient's ability to maintain eye position while scanning. Further, the positioning of the transducer, due to the spherical shape of the cornea, remains orthogonal to the surface of the cornea and thus achieves a maximum echo return signal. Accordingly, the invention enables an ultrasound eye examination procedure to be carried out without the use of a complex mechanical scan system. It is further useful for the imaging of various eye pathologies, such as corneal scars, tumors, cysts, glaucoma, hypotony and trauma.

It should be understood that the foregoing description is only illustrative of the invention. Various alternatives and modifications can be devised by those skilled in the art without departing from the invention. For instance, the methods described above can be employed with various eye scanning techniques, especially those affected by the specularity of the cornea, such as Coherence Tomography and slit lamp modalities. Accordingly, the present invention is intended to embrace all such alternatives, modifications and variances which fall within the scope of the appended claims.

We claim:

1. Apparatus for ultrasonically examining a patient's eyes, wherein a patient's first eye to be imaged is submerged in a liquid bath, said apparatus comprising:

a fixed ultrasound transducer in contact with said liquid bath, for directing a beam of ultrasound energy to said first eye and for receiving echoes of said ultrasound energy;

fixation source means juxtaposed to a second eye of said patient, for displaying a fixation target; and control means for operating said fixation source means to move said fixation target relative to said second eye while said patient moves said second eye to remain focused on said fixation target, movement of said second eye causing said first eye to move concurrently and enabling relative movement between said beam of ultrasound energy and anterior segments of said first eye.

2. The apparatus as recited in claim 1, wherein said fixation source means comprises:

a fixation target display coupled to said control means;

imaging means coupled to said control means;

optical means positioned between said second eye and said fixation target display for projecting an image of said second eye onto said imaging means while said fixation target display is operated to move said fixation target, whereby data from said image of said second eye is employed by said control means in conjunction with said data from said echoes to image said anterior segments of said first eye.

3. The apparatus as recited in claim 1 wherein said fixation source means is a light-emitting diode array.

4. The apparatus as recited in claim 1 wherein said fixation source means is a video monitor.

5. The apparatus as recited in claim 1 wherein said fixation source means and ultrasound transducer are positioned on a pair of goggles to be worn by a patient.

6. A method for ultrasonically examining a patient's eyes, wherein a patient's first eye is submerged in a liquid bath, said method comprising the steps of:

positioning a fixed ultrasound transducer in contact with said liquid bath and directing a beam of ultrasound energy therefrom to said patient's first eye;

receiving echoes of said ultrasound energy;

displaying a fixation target that can be viewed by a second eye of said patient; and moving said fixation target relative to said second eye, while said patient moves said second eye so as to remain focused on said fixation target, movement of said second eye causing said first eye to move concurrently with said second eye and enabling relative movement between said beam of ultrasound energy and anterior segments of said first eye.

7. The method as recited in claim 6, comprising the further steps of:

projecting an image of said second eye onto an imaging means while said fixation target is moved; and providing data from said image of said second eye and data from said echoes to a processor to enable imaging of anterior segments of said first eye.

8. The method as recited in claim 6 wherein said moving of said fixation target is created by a scanning of a light-emitting diode array.

9. The method as recited in claim 6 wherein said moving of said fixation target is created by a scanning of an image on a video monitor.

\* \* \* \* \*